United States Patent [19]

Martin

[11] Patent Number: 4,715,386

[45] Date of Patent: * Dec. 29, 1987

[54] COMPUTER-AIDED DRUG-ABUSE DETECTION

[75] Inventor: Peter G. Martin, Mercer Island, Wash.

[73] Assignee: National Patent Analytical Systems, Inc., New York, N.Y.

[ * ] Notice: The portion of the term of this patent subsequent to Mar. 18, 2003 has been disclaimed.

[21] Appl. No.: 839,614

[22] Filed: Mar. 14, 1986

[51] Int. Cl.⁴ .............................................. A61B 5/04
[52] U.S. Cl. .................................... 128/733; 364/417
[58] Field of Search ................. 128/733, 630; 364/417

[56] References Cited

U.S. PATENT DOCUMENTS 3,809,069  5/1974  Bennett ................................ 128/731
4,576,184  3/1986  Westerman .......................... 128/733

Primary Examiner—Kyle L. Howell
Assistant Examiner—John C. Hanley
Attorney, Agent, or Firm—Hopgood, Calimafde, Kalil, Blaustein & Judlowe

[57] ABSTRACT

The invention contemplates computer-aided analysis of recorded electronystagmograph data for a subject who is suspected of drug ingestion. The reference base for the analysis is predetermined by first entering into computer storage digital data that are characteristic of each of a selected plurality of component features of time-varying fluctuations in electronystamograph waveforms for each of a plurality of different ingested drugs, wherein the selected component features exist within a standardized set of at-rest conditions of electronystagmograph measurements. The plurality of component features is selected such that each of the drugs is characteristically identifiable by the presence of its singular combination of said component features. The subject's time-varying fluctuations in electronystagmograph waveforms are non-invasively measured and digitally recorded, for each of the at-rest conditions of the standardized set; and the subject's digitally recorded waveform is compared with the digitally stored reference data for each of the component features to ascertain the existence vel non of any correlation therebetween, thereby enabling determination as to whether a particular drug-identifying combination of the component features exists.

25 Claims, 12 Drawing Figures

FIG. 3.
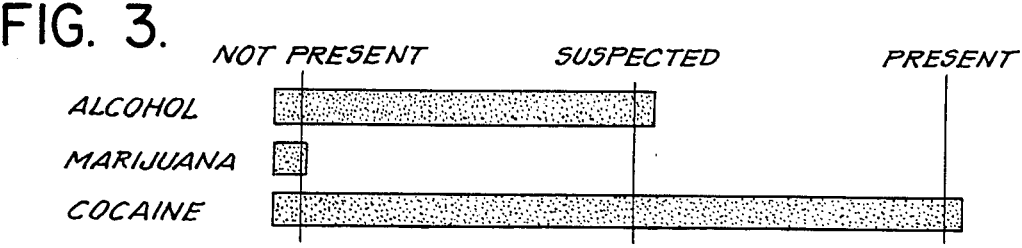
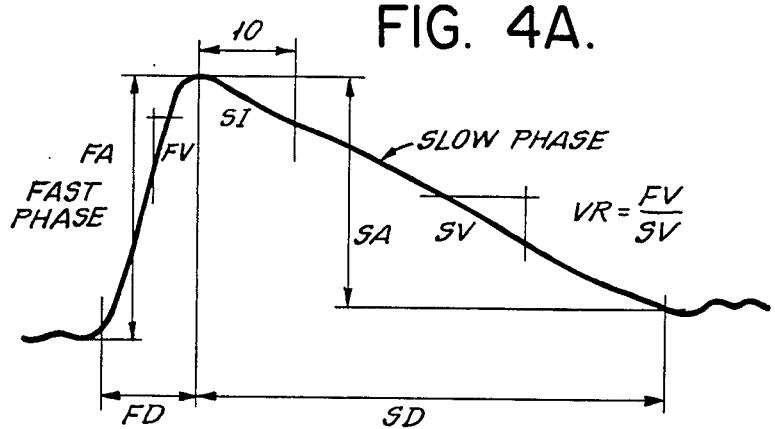
FIG. 4A.
FIG. 4B.
FIG. 4C.
FIG. 5A.
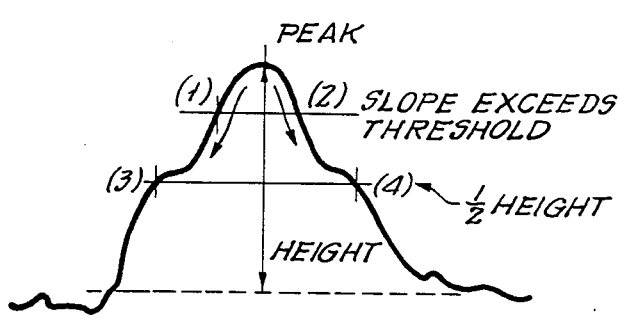
FIG. 5B.
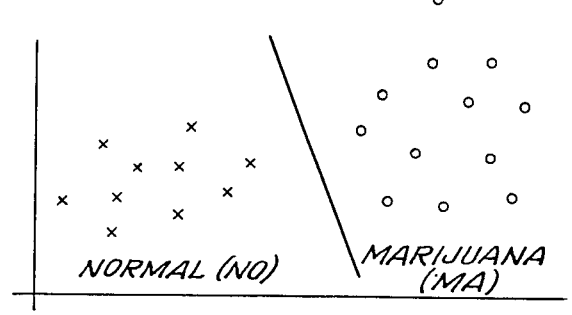
FIG. 6A.
FIG. 6B.
FIG. 6C.
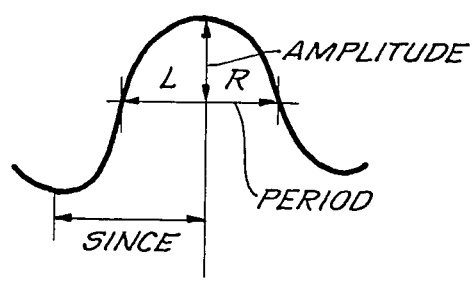

COMPUTER-AIDED DRUG-ABUSE DETECTION

BACKGROUND OF THE INVENTION

The invention relates to computer-aided means for detecting drug ingestion based upon the effects of drugs on electronystamograph waveforms.

Westerman, pending patent application, Ser. No. 603,243, filed Apr. 23, 1984, discloses a method for drug-abuse detection, using an electronystamograph (ENG) machine (a) to determine a plurality of reference electronystamograph waveforms, respectively corresponding to waveforms individually reflecting independent ingestion of each of a plurality of drugs, (b) recording a subject's waveform while the subject is subjected to a static positional test, and (c) comparing the subject's measured waveforms with the reference waveforms to determine which drug or combination of drugs was ingested by the subject. Each of the reference waveforms is obtained by having a person who is known to be free of drugs ingest a predetermined dose of a particular drug, and as to each such person a recording is made of resulting CRP waveforms, for reference purposes.

The indicated technique calls for much expertise and alert judgment on the part of the operator, to a degree enabling but a select few to make the waveform comparison and judgment with requisite accuracy. Moreover, the time taken even by the expert may be too great, for a desired context of use by law-enforcement personnel.

BRIEF STATEMENT OF THE INVENTION

It is, accordingly, an object of the invention to provide an improved method and means for detection of drug ingestion, to the end that a particular ingested drug (or drugs) is identified, objectively and more rapidly than heretofore.

A specific object is to achieve the above object using computer-aided analysis of recorded electronystamograph data for a subject who is suspected of drug ingestion.

The invention achieves these objects by first entering into computer storage digital data that are characteristic of each of a selected plurality of component features of time-varying fluctuations in an electronystamograph waveform for each of a plurality of different ingested drugs, wherein the selected component features exist within a standardized set of at-rest conditions of electronystamograph measurements. The plurality of component features is selected such that each of the drugs is characteristically identifiable by the presence of its singular combination of said component features. The subject's time-varying fluctuations in electronystagmograph waveforms are non-invasively measured and digitally recorded, for each of the at-rest conditions of the standardized set; and the subject's digitally recorded waveform is compared with the digitally stored reference data for each of the component features to ascertain the existence vel non of any correlation therebetween, thereby enabling determination as to whether a particular drug-identifying combination of the component features exists. Reliance is placed on statistical evaluation of redundant component features (events) in the subject's recorded measurements.

DETAILED DESCRIPTION

The invention will be described in detail, with reference to the accompanying drawings, in which:

FIG. 1 is a block diagram schematically indicating apparatus of the invention;

FIG. 2, being the composite of FIGS. 2A and 2B, interconnected at points x, y, z, is a more detailed schematic diagram of circuit-board components added to a commercial personal computer forming part of the apparatus of FIG. 1;

FIG. 3 is an illustrative display of a reported analysis to identify one as against two other drugs in an analysis pertaining to the invention;

FIGS. 4A, 4B and 4C are graphs illustrative of an analysis for alcohol;

FIGS. 5A and 5B are graphs similarly illustrative for a marijuana analysis; and

FIGS. 6A, 6B and 6C are graphs similarly illustrative for a cocaine analysis.

Figure 1:
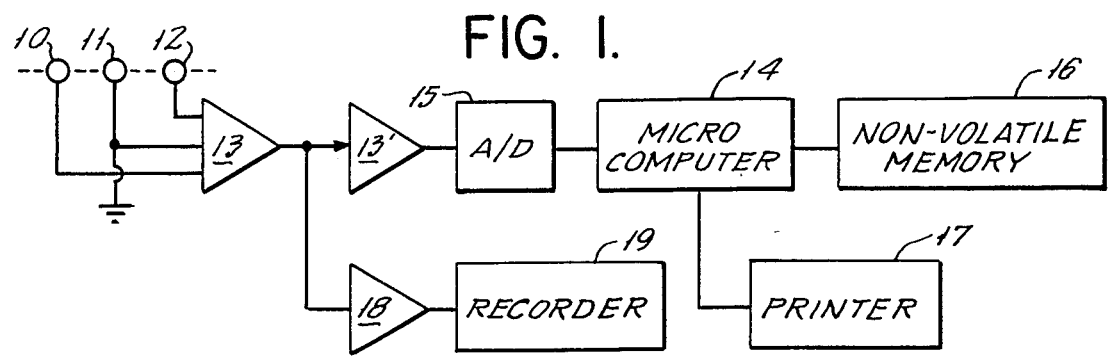

In FIG. 1, apparatus of the invention is shown generally to comprise an ENG machine having three facial electrodes 10-11-12, with leads to pre-amplifier means 13, and digital-computer means 14 connected to the output of means 13 via analog/digital converter means 15. A non-volatile memory 16 (for security, identification and like purposes) and indicator means 17, such as a printer, are associated with the computer means 14, which may be an IBM-PC, a Panasonic Senior Partner, or the like. In use, a grounded electrode (11) is applied to the forehead, and the other two electrodes are applied to the right and left temples of a given individual subject. Although not necessary to the invention, FIG. 1 additionally shows an amplifier 18 and chart recorder 19 functioning from the preamplifier output consistent with the disclosure of said Westerman patent application, for the possible purpose of checking out performance of the invention.

More specifically, dashed lines to and between electrodes 10-11-12 schematically indicate that all electrodes are components of a plastic headband, each electrode providing Ag-AgCl skin contact for picking up low-level ENG waveforms from the subject. The amplifier means 13 amplifies these waveforms about 7,000 times; and means 13 includes provisions for protecting the subject from accidental electric shock, and for assuring that the electrodes have a good "hook-up". For security and identification purposes, the non-volatile memory 16 will be understood to store customer or serial-number identification and to provide a count of how many times the system's software is used, thereby providing a use measurement, for billing purposes; the non-volatile memory may also include provision for accumulating a data base, i.e., entering individual drug determinations as accretions to a data base, for each specific drug, in order to accumulate statistics or trends of specific drug use. Whatever the make of computer means 14, it will be presumed, for purposes of presently described use of the invention, to be a microcomputer based on the 8088 processor chip, with at least 256k bytes of user memory and one 5.25-inch diskette drive, and means 17 may be a dot-matrix printer which, in the case of the Panasonic Senior partner is a built-in component. The operating system is MS-DOS, version 2.0 or later, and operating software, in object-code format, is supplied on a diskette.

Before proceeding with more detailed description, it will be useful to realize that, upon completion of the taking and computer analysis of standardized ENG-waveform measurements on a given subject, as after arrest on suspicion of drug ingestion, the print-out at 17 will state the drug present, for example, marijuana, as well as tabulating relevant data such as the run number, date and time, as well as the subject's name, date of birth, sex and driver's license number; further data such as the arresting agency and location, and run technical data may also appear on the print-out.

Figure 2A:
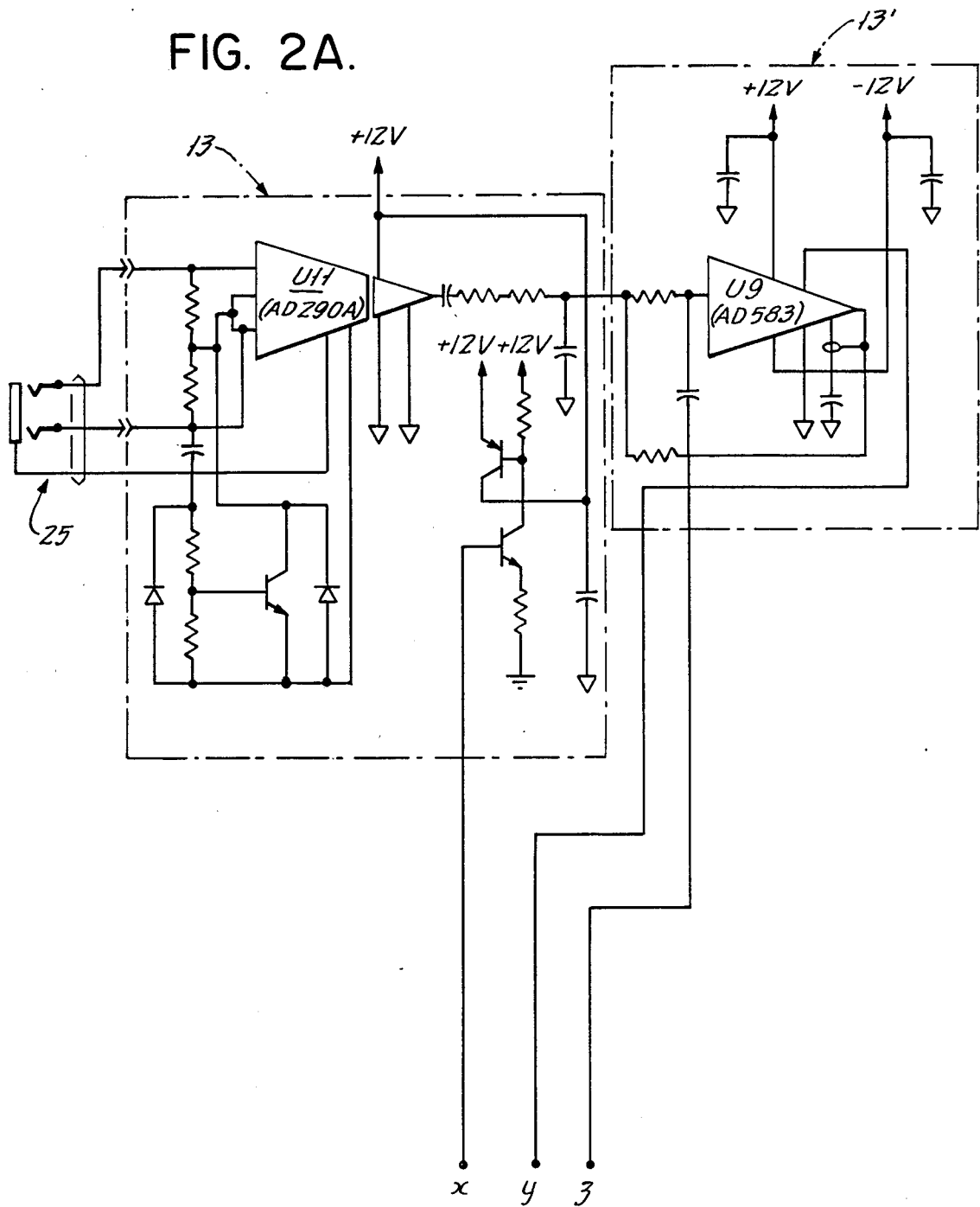
Figure 2B:
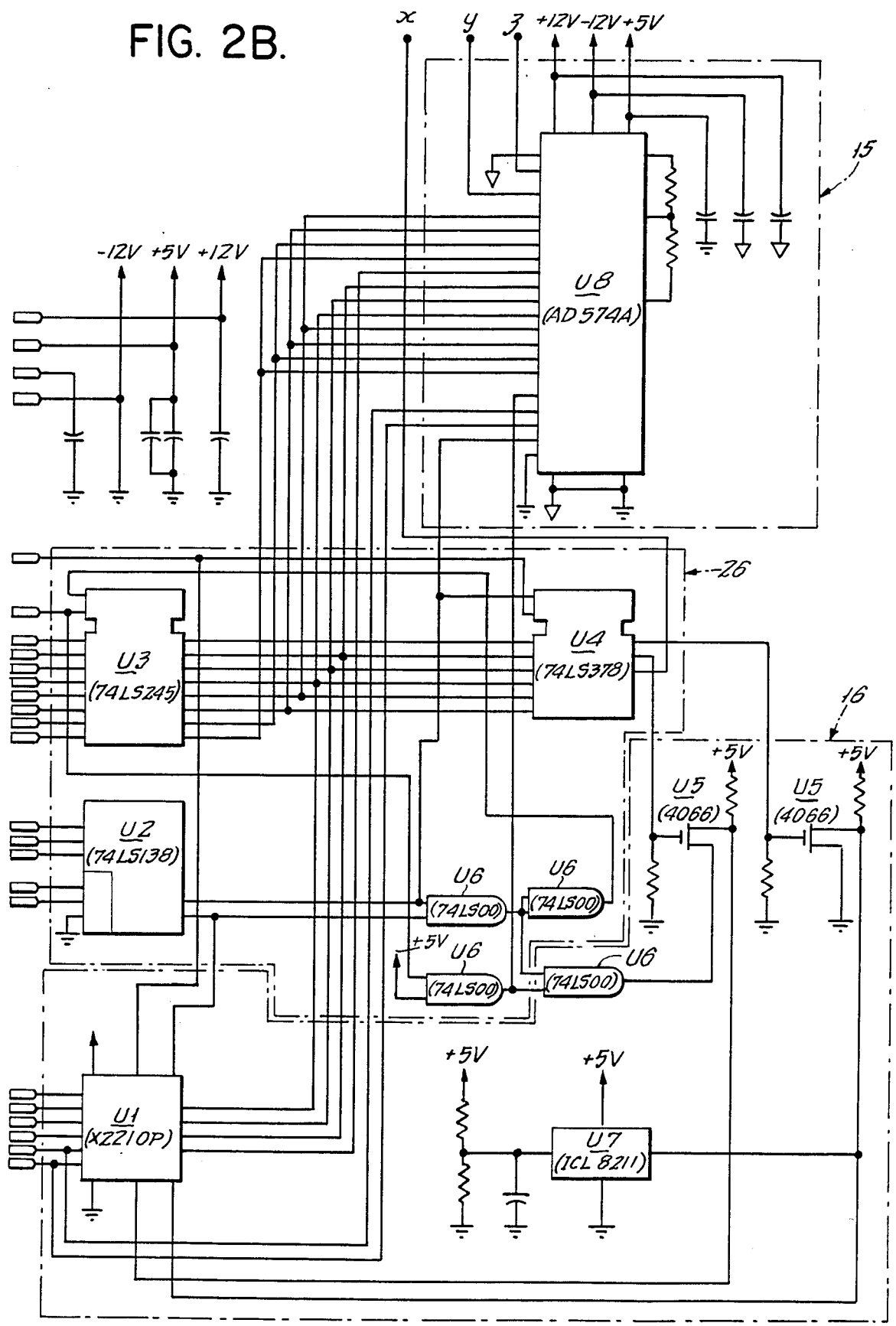

More specifically as to circuitry, reference is made to the schematic diagram of FIG. 2, for a generalized showing of components of a A/D circuit board which is added to an IBM PC-compatible computer to enable operation of the invention; for example, this board fits into a slot on the card rack of the Panasonic Senior Partner, and it is wired to a phono jack 25 mounted through the front panel of the computer; the headband of electrodes 10-11-12 has a cable connected plug to fit the jack 25. Signals from the electrodes are in the range of 10 to 200 microvolts.

Briefly, the A/D board of FIG. 2 comprises four parts.

—a high-gain biological amplifier 13—13', which amplifies and filters the signals picked up from the test subject, before processing by the A/D converter; safety circuitry associated with the biological amplifier assures that the test subject cannot be exposed to leakage currents in excess of a few microamperes;

—a 12-bit analog-to-digital converter 15 (U8) for translating analog waveforms collected from test subjects into a machine-readable digital format;

—the non-volatile memory device 16 for securely storing information such as accretions to a system-usage counter, even when computer power is turned off; and —address-decoding logic and a peripheral controller, generally indicated at 26.

The first or preamplifier stage 13 of the biological amplifier is designed for low input currents, low input offset voltage, high common-mode rejection ratio, and high power-supply rejection ratio. It is suitably and illustratively based on the Analog Devices Model 290A single-channel isolation amplifier (U11). Test-subject safety is assured by the internal design of the isolation amplifier.

The second stage 13' of the biological amplifier combines the functions of (a) an amplifier with a gain of 70, (b) an active filter with a 0.05 to 11-Hz bandwidth, and (c) a sample-and-hold circuit for the analog/digital conversion process. This part of the amplifier is suitably based on Analog Devices Model AD583 IC sample-and-hold gated operation amplifier, and since signals from the electrodes are in the indicated microvolt range, grounding is critical, being shown in FIG. 2 by triangular symbolism for the analog ground planes and by shading for the digital ground plane, to the end that noise pick-up shall be minimized.

The 12-bit analog-to-digital converter 15 (U8) is suitably Analog Devices Model AD574A. And the address-decoding logic provides an interface between described and indicated circuits and the bus of the computer, using techniques well known in the art.

Software for operating the invention relies on suitable algorithms for distinguishing drug (ENG) waveforms from normal (ENG) waveforms, and it is helpful first to discuss presently preferred methodology used for the development of drug-detection algorithms. This methodology falls into the area of artificial intelligence known as "expert systems", an expert system being a computer which has been programmed to emulate the skills and knowledge of a human expert in a particular field or domain; the preferred embodiment reflects the expertise of two individuals, namely, Dr. Westerman, the inventor in said copending patent application, and his assoiacte, Liane M. Gilbert.

The presently preferred expert approach first categorizes ENG waveforms of a given run into one of three groups, namely:

drugs inducing nystagmus events, namely, marijuana and alcohol (and pathology);

drugs inducing large pendula events, namely barbiturates, tranquilizers, and amphetamines; and drugs creating events concentrated near the baseline, namely, cocaine, hallucinogens, and opiates.

The first drug group produces drug nystagmus in ENG waveforms, i.e., saccadic movements in one direction, followed by a linear return to the baseline. The second group produces pendula waveforms, with large amplitude signals of roughly sinusoidal shape. The last group comprises the baseline drugs, which tend to suppress the waveform and to produce various events near the baseline.

Overview, for Drug Segreqation

An overview* of the inventive technique for segregating basic drugs and drug categories is provided by a set of decision rules, showing how each drug is distinguished over the others; these rules appear from the following tabulation of screening-question steps:

*This overview is followed below by first and second levels of algorithm statement, for each of several specific drugs.

Step 1. Does analysis of the waveform show:
(a) activity close to the baseline?
   If yes, the indication is NO (normal), OP (opiate), CO (cocaine), or HA (hallucinogen); go to Step 2.
(b) several nystagmus events?
   If yes, the indication is PA (pathology), AL (alcohol), or MA (marijuana); go to Step 3.
(c) large pendula movements away from the baseline?
   If yes, the indication is AM (amphetamine), TR (tranquilizer), or BA (barbiturate); go to Step 4.

Step 2. To resolve one from the group NO, OP (opiate), CO (cocaine) or HA (hallucinogen), analyze the waveform to determine whether it has a 5-6 Hz "buzz" activity.
(a) If yes; HA (hallucinogen) has been identified.
(b) If no, the indication is NO (normal), OP (opiate), or CO (cocaine); go to Step 5.

Step 3. To resolve individual conditions within the group PA (pathology), AL (alcohol) or MA (marijuana), analyze the waveform to determine whether it is characterized by:
(a) several nystagmus with the following characteristics:
   1. mostly "heads"*;
   2. mostly with a period of 0.5 to 3 secs;
   3. mostly in the PAN position;
   4. slow-phase returning consistently toward the baseline;
   5. tendency to exponential decay in the slow phase (shape < 100);
   6. tendency toward noise in the slow phase; and
   7. waveform "leaning" in direction of the head.

if all of these characteristics are present, then AL (alcohol) has been identified.

*"Heads" and other terms listed in the present overview are later defined.

(b) many saccades with the following characteristics:
1. mixed "heads" and "tails";
2. mostly with a period of 0.5 to 5 secs;
3. new saccades often interrupting the slow-phase of the previous one;
4. slow-phase often not returning to the baseline;
5. tendency to straight-line slow phase (shape~100);
6. tendency toward no noise in the slow phase; and
7. waveform having "mountainous shapes", or not "leaning" in either direction.
    If all these characteristics are present, then MA (marijuana) has been identified.

(c) several nystagmus (mostly left or mostly right, but not all occurring in a single run), and waveform "leaning" either left or right.
    If these characteristics are present, then a pathological problem has been indicated.

Step 4. To resolve one from the group (AM) (amphetamine), TR (tranquilizer) or BA (barbituate), analyze the waveform for the presence of triangular movements?
(a) If yes, TR (tranquilizer) has been identified.
(b) If no, go to Step 6.

Step 5. To resolve one from the group NO (normal), OP (opiate) or CO (cocaine), analyze the waveform for a tendency toward flat spots, with small rapid movements in between?
(a) If yes, OP (opiate) has been identified.
(b) If no, go to Step 7.

Step 6. To resolve as between AM (amphetamine) and BA (barbiturate), analyze the waveform for:
(a) much mid- or high-frequency noise superposed on much low-frequency activity.
    If yes, BA (barbiturate) has been identified.
(b) much low-frequency activity free of noise, or a tendency to lean in either direction.
    If yes, AM (amphetamine) has been identified.

Step 7. To resolve as between NO (normal) CO (cocaine), analyze the waveform for presence of bimodal (combined low- and mid-frequency) ripples.
(a) If yes, CO (cocaine) has been identified;
(b) If no, it has been determined negative as to CO (cocaine).

It is noted that the foregoing tabulated analysis assumes that the search is for a single drug; however, software actually runs algorithms for all drugs in parallel, so that drug combinations are not excluded by performing the above analysis. It is also noted that the terms such as "heads", "tails", "slow phase", "leaning", "triangular", and "flat spots" appear in this tabulation; these terms will be explained in connection with illustrative algorithms, specific to various of the tabulated steps.

It should be understood that any description of an algorithm is only as presently (i.e., currently) preferred, in that the invention is still developmental, and changes reflect improvements made to system accuracy. The presently disclosed algorithms should therefore be regarded as representative of techniques used, in that other algorithms of at least equal effectiveness may be developed for each drug.

It should also be understood that the algorithms to be described rely, for greatest effectiveness, on consistency of the scale of eye deflection, and that in the present state of the art with respect to electrical resistance of ENG-electrode contact with the subject, it is recommended that a calibration run be initally made on the subject to enable a corrective gain adjustment in the system, whereby all waveforms from any given trial of a particular subject have the same scale, in "counts" per degree of eye deflection. For the calibration run (tasking), the subject is asked to follow a light spot on the computer screen; the spot is deflected alternately left and right from an initial center position, while the subject's head is positioned such that his eye deflection is ±10 degrees (e.g., eyes 18 inches from the screen). The analog/digital converter* 15 presently used in operating the invention produces outputs in the range −2047 to +2047, and the calibration procedure sets the gain so that a ±10 degree eye deflection yields an output of ±700 counts, i.e., 70 counts per degree. The dynamic range of the system is therefore a little less than ±30 degrees. Each ENG waveform comprises 1024 data points, collected 30 times per second over a 34-second period, and references herein to the amplitude of events in waveforms are in units of "counts" of eye deflection**.

*Analog Devices Model AD574A, being a 12-bit A/D converter with microprocessor interface. ** It is noted that the ENG waveform contains signal components unrelated to eye movement, such as brain waves. Thus, the present discussion of calibration is in terms of degrees-of-eye-movement equivalence. The exact sources of signals in an ENG waveform are unknown, but the absence of this knowledge has no effect on the performance of the system or method of the invention, it being sufficient to know that the drug-specific waveforms exist.

The algorithms to be described rely on a set of four ENG waveforms taken for the same subject, in addition to the calibration run described above. These four waveforms are for the following positions of the subject:
In a sitting position,
    (1) eyes closed, right
    (2) eyes closed, left
While lying down, with the head turned to place an ear against a supporting surface (i.e., PAN position)
    (3) right, eyes closed,
    (4) left, eyes closed.

These four runs are calibrated to match the 70 counts/-degree figure noted above, and the thus-calibrated runs are entered into digital storage, for availability as needed for use of various drug-identifying algorithms.

In the nystagmus group, alcohol, marijuana and certain pathologies produce nystagmus events in ENG waveforms, but these three conditions can be distinguished, as follows:
    If more than a defined percentage of nystagmus are RIGHT or LEFT, then a pathological condition is indicated;
    Otherwise, if more than a defined percentage of nystagmus are HEADS, then alcohol is indicated;
    Otherwise, for intermediate results, marijuana is indicated.

In the above situations, RIGHT and LEFT mean that the saccadic movements are to the right and left, respectively, regardless of the subject's test position, for taking the involved ENG waveform. HEADS means that the saccadic movements are in the same direction with respect to the test position (e.g., to the left, in the PAN left position); TAILS means that the saccadic movements are in the opposite direction with respect to the test position (e.g., to the right, in the PAN left position).

Although the events produced by these three nystagmus situations are similar, different algorithms have been developed for alcohol and for marijuana; a satisfactory algorithm for pathology detection has yet to be developed, because emphasis to date has been on drug identification as an element of highway-safety law enforcement.

Generalized Discussion of Individual Drug Algorithms

The currently preferred alcohol algorithm depends on two straightforward software routines which detect the presence of (a) leaning; and (b) slow phases in a waveform. By "leaning" is meant a tendency for a waveform to spend less time moving in one direction than the other, as would occur with drug nystagmus events predominantly in one direction. The leaning is measured by computing the ratio of left-moving to right-moving changes occurring in the 1024 data points of a waveform. If the ratio is greater than one, then the eye is spending more time moving left than moving right. This can only occur if the waveform comprises rapid movements to the right, interspersed with slow movements to the left. The effects of random noise in the signal are removed by measuring the direction change over three data points; without this precaution, most waveforms would exhibit leaning close to unity.

The term "slow phases" refers to the drift back to the baseline after a saccadic movement. The drift velocity (in counts per data point) falls into a specific range for alcohol-induced events. A data point is said to be in a slow-phase event if its velocity is in the range 10 to 60 counts per data point. Again, the effects of random noise are reduced by measuring the slow-phase velocity over three data points.

It has been determined experimentally that alcohol can be reliably predicted if the number of slow-phase data points is more than 280; and if the leaning ratio is greater than 1.045 in the PAN-right position, and less than 0.895 in the PAN-left position. These rules alone are sufficient to achieve alcohol accuracies in the 90's percent.

These two routines are good examples of simple, fast and direct methods for measuring alcohol-induced events. The methods currently used in the detection of other drugs tend to be more complex, and slower.

Subject to certain criteria, the marijuana algorithm makes use of five measurements on the standardized set of four waveforms for a given subject:
 the number of nystagmus events;
 the number of saccade events;
 the average amplitude of two runs having the largest individual average signal amplitudes;
 the ratio of the number of nystagmus events to the number of saccade events; and
 the mean signal amplitude for all four of the runs.
The measurement of slow-phase data points is the same as in the alcohol algorithm. Leaning ratio is not important because marijuana does not exhibit a consistent leaning in one direction; saccadic events typically occur in both left and right directions in all test positions. The mean signal amplitude is simply the average distance of each data point from the baseline; low values are associated with baseline drugs, while high values are associated with more active drugs such as marijuana.

The ratio of saccade-to-nystagmus events is more complex. A saccade may or may not be followed by drift back to the baseline; if it is, the event is labelled a nystagmus. In alcohol, most saccades are associated with nystagums, but in marijuana this is less so, because a saccade may be followed by a relatively flat period, or by another saccade in either direction.

A saccade is defined as a velocity of more than 80 counts per data point, as measured over three data points. The end of the saccade is defined as the first point where the velocity falls back below 80. The events after each saccade are examined to see if they meet the requirements for a nystagmus, as follows:
 Fast amplitude, 325 to 1700;
 Fast duration, less than 9;
 Fast velocity, greater than 75;
 Slow-phase amplitude, greater than 100;
 Slow-phase duration $\geq$ 10;
 Slow-phase velocity, 3 to 30;
 Initial slow-phase velocity, less than 30;
 Shape, 70 to 140; and
 Velocity ratio, 3 to 50.
The fast-phase amplitude is measured from starting to ending data points of the saccade; small amplitudes are usually not drug-related, and large events are often eye blinks and other aberrations. The fast duration is the number of data points between the start and end of the fast phase; large duration events are usually not drug-induced. The fast velocity is the average eye velocity during the fast phase, as defined by the fast amplitude, divided by the fast duration; most drug induced involuntary eye movements have velocities greater than 75. A true nystagmus will normally exhibit a slow phase which returns approximately to the baseline; if the slow-phase amplitude is less than 100, then the event is assumed not to be a nystagmus. The slow-phase duration is usually more than 10 data points in the case of a nystagmus; this is measured from the peak of the saccade to the end of the slow phase, and the end of the slow phase is defined as a new saccade in either direction, subject to a maximum slow-phase duration of 60 data points (two seconds). The slow-phase velocity is measured in the same manner as for the fast phase; values less than 3 are deemed to be flat (or in the wrong direction); values greater than 30 are uncharacteristic of nystagmus. The initial slow-phase is also measured over the first 10 data points after the saccade peak; this helps identify events which look like a nystagmus except for an abnormal peak shape (e.g., a brief saccadic movement before the true slow phase commences).

The shape of the slow phase distinguishes an essentially straight line from an exponential decay, or (less likely) a line whose slope increases with time. The algorithm compares the area under the slow-phase curve with that of a straight line drawn from the saccade peak to the end of the slow phase. A shape of 100 indicates a straight line, and values under 100 indicate an exponential decay. A drug nystagmus rarely exhibits a pronounced exponential decay.

Velocity ratio is the ratio of fast-phase velocity to slow-phase velocity; for a drug nystagmus, these are typically in the range 3 to 50.

The cocaine algorithm is based on the detection of sinusoidal pulses or ripples in the waveform. Sometimes, the waveform is "bimodal", with ripples of two frequencies superimposed on top of each other. Ripple frequencies are lower than for hallucinogens.

Events with a characteristic frequency range are often detected by the use of fast Fourier transforms (FFT), which provide an amplitude versus frequency measurement of a waveform. For example, an FFT might indicate an amplitude peak at a frequency of 3 Hz due to some underlying event. In reality, the events used in the visual interpretation of cocaine waveforms can be much smaller than other, non-drug related, events. The signal-to-noise ratio is very poor, and peaks of FFT graphs are not readily discernable. This problem is compounded by the broad range of characteristic frequencies involved (roughly 1 to 3 Hz).

On the other hand, the currently preferred cocaine algorithm processes ENG waveforms to identify sinusoidal events in the waveform by direct measurements on the amplitude-versus-time signal. One consideration in determining this preference is that many normal waveforms exhibit some sinousoidal events, but only cocaine will show such events consistently throughout most of the waveforms collected from a test subject. Another consideration is to maximize the signal-to-noise ratio when saccades occur in the waveform, in addition to the cocaine events. This is achieved by detecting saccades, and by then cancelling them out of the waveform. This process, in combination with a high-pass filter yields an essentially flat waveform containing only frequency components above about 0.5 Hz, which is then analyzed for cocaine.

The cocaine algorithm is based on analyzing reversals (pulses) in the thus-processed waveform, which reversals have amplitudes of more than 40, i.e., the hysteresis of a tracking algorithm is set to 40. When any such event is detected, the preceding pulse is measured, and the average measurements for the events in a waveform are compared with values associated with cocaine waveforms. The following pulse characteristics are measured:

- Time since previous event (mean=7 to 19 counts)
- Amplitude of pulse (mean=43 to 101 counts)
- Width of pulse (mean=4.5 to 16 counts)
- Reversals within the pulse (mean=1.6 to 3.6 counts)
- Ratio of left/right pulse areas (mean=0.99 to 1.48 counts)
- Shape of pulse (mean=0.57 to 0.63 counts)

The cocaine algorithm also computes the spread of these parameters, that is, the standard deviation divided by the mean. A low spread indicates a high degree of consistency in events in a waveform. The limit values are as follows:

- Time since previous event (spread=0.63 to 1.19 counts)
- Amplitude of pulse (spread=0.47 to 1.57 counts)
- Width of pulse (spread=0.56 to 1.45 counts)
- Reversals within the pulse (spread=0.84 to 1.07 counts)
- Ratio of left/right pulse areas (spread=0.49 to 0.87 counts)
- Shape of pulse (spread=0.16 to 1.16 counts)

In order to minimize the effects of random noise, the original waveform is smoothed by making each data point the mean of itself and the following data point. Reversals within a pulse are defined as any reversal in direction with an amplitude more than 10 percent of the hysteresis (4 counts). The ratio of left/right pulse areas provides a measure of the symmetry of the pulse, which should be close to unity for sinusoidal events. The shape of the pulse is the area under the curve as a fraction of what would be expected for a square pulse of the same amplitude; for a pure half-sine-wave pulse, the expected value is 0.7071.

Opiate algorithm. The primary distinction of opiates over other drugs is the tendency for the waveform to be "frozen" at a particular level for a fraction of a second, many times through a trial. The software includes an algorithm for detecting this behavior.

Hallucinogen Algorithm. LSD and other hallucinogens induce a high-frequency ripple on the waveform, with a characteristic frequency of 5 to 6 Hertz. This characteristic is not found in any other drugs, and the hallucinogen-detecting software includes an algorithm for detecting this specific and narrow frequency range.

SPECIFIC IN-DEPTH EXAMPLES OF INDIVIDUAL DRUG ALGORITHMS

A better appreciation of the invention follows from a description of its use in differentiating between alcohol, marijuana and cocaine, through software-directed analysis of a given subject's recorded and calibration-corrected four runs (two sitting, and two lying down for PAN right and PAN left), wherein the result of the analysis is displayed both on the screen of computer 14 and by printed report at 17, in a bar-chart format as illustrated in FIG. 3. Thus, for this illustrative case, the displayed and printed report will contain specific commitment as to each of the three drugs, with qualification as to whether the drug is "not present", "suspected", or "present". The bar chart of FIG. 3 shows a subject with alcohol "suspected" and cocaine "present", and with no marijuana detected. The "present" result means that the drug was found with less than 1 percent chance of error; while the "suspected" result means that the drug was found with less than 5 percent chance of error, thus indicating a recommendation for further testing, e.g., a blood analysis.

Alcohol detection proceeds using all of the four standardized runs, once they have been calibrated to 70 counts/degree of eye deflection. Next, saccade and nystagmus events are detected and their statistics collected, and finally the results from all four runs are combined to effect a single conclusion.

More specifically, and with reference to the sample saccade event depicted in FIG. 4, the onset of a saccade is recognized when a velocity greater than 60 counts/sample occurs when averaged over three data points; having achieved such recognition, the software program assures that the waveform is tracked, point by point, until either (a) the direction reverses, or (b) the velocity falls to less than 25 percent of the maximum seen since the event started. This determines the start and finish of a rapid event and, therefore, its fast duration (FD), fast amplitude (FA), and fast velocity (FV). The program now tracks the slow phase of the event until either (a) another fast movement begins, or (b) a two-second time-out expires. This determines the slow duration (SD), slow amplitude (SA), and slow velocity (SV). The event is now counted as a saccade if FD<8 and SD>6. The program keeps count of saccades which are (a) "heads" (i.e., in the same direction as the head is turned), (b) "tails" (namely, in the direction opposite to heads), (c) "left" and (d) "right".

The program next checks as to whether the event also qualifies as a nystagmus. First, the initial slow-phase velocity (SI) is measured; this is the average velocity in the first 10 data points in the slow phase. Next, the velocity ratio VR (i.e., FV/SV) is computed, and finally the SHAPE of the slow phase is computed. If SHAPE = 100, then the slow phase is a straight line; if SHAPE is<100, then it is concave (see FIG. 4A), and if SHAPE is>100, then it is convex (see FIG. 4B).

The nystagmus check is in two steps. First, the values FA, VR, SHAPE and SI/FA are used independently to determine the probability that the event is alcohol-induced, based on the statistics for known alcohol waveforms. A normal distribution is assumed for each parameter, with the following values of mean and standard deviation:

| Parameter | Mean | Standard Deviation (SD) |
|---|---|---|
| FA | 600 | 220 |
| VR | 5.9 | 3.2 |
| SHAPE | 92 | 12 |
| SI/FA | 0.06 | 0.025 |

Next, these probabilities are combined according to:

$$P_{Nyst.} = 100 * \sqrt[6.5]{P_{FA} * P_{VR} * P_{SHAPE} * P_{SI/FA}},$$

the root 6.5 being used so that if each parameter is one standard deviation from the mean, $P_{Nyst.}$ will be 50 percent.

As with saccades, the program counts how many nystagmus are heads, tails, left and right.

In addition to checking events to see if they meet the criteria for saccades and nystagmus, the following gross measurements are made on the waveform:
  (a) Mean absolute amplitude of the signal;
  (b) The "leaning factor", namely, the ratio of time spent moving right vs. time spent moving left, where "moving" means a velocity $\geq 10$ counts/sample; and
  (c) The "slow time", namely, the maximum of right- or left-moving times, as seen in waveforms for the PAN positions only.

The final alcohol determination is made if all the following conditions are true:
  (a) Number of "heads" saccades in PAN positions is $>5$;
  (b) Number of "tails" saccades in PAN positions is $\leq 4$;
  (c) Number of "tails" nystagmus in PAN positions is $\leq 2$;
  (d) Mean amplitude for all four runs $>80$;
  (e) Leaning factor in eyes closed, right position $\geq 0.9$;
  (f) Leaning factor in PAN-right position $>1.02$;
  (g) Leaning factor in PAN-left position $<0.89$;
  (h) Slow time $\geq 230$ in PAN positions; and
  (i) Number of tails saccades, times 4.5, is $\leq$ number of heads saccades in PAN positions.

If the foregoing conditions are all true, alcohol is reported as suspected; and if the slow time is $\geq 300$, and the number of "heads" saccades in the PAN position is $>8$, then alcohol is reported as present.

Marijuana detection follows from an algorithm which is similar to that for alcohol detection, since both drugs induce saccadic events. The differences are:

A marijuana event begins when the velocity exceeds 90 counts, as distinguished from the 60 counts/sample for alcohol detection.

A marijuana event must have FD$<8$, SD$>2$, and an absolute value of FA in the range 250 to 1000, in order to be counted as a saccade.

A marijuana nystagmus must satisfy the criteria:

$$325 \leq |FA| \leq 1700$$

$$FD \leq 9$$

$$75 \leq |FV|$$

$$100 \leq |SA|$$

-continued $$10 \leq SD$$

$$3 \leq |SV| < 30$$

$$|SI| < 30$$

$$70 \leq SHAPE < 140$$

$$3 \leq VR < 50$$

$$0 \leq |SI/FA| \leq 0.09$$

In addition, the marijuana algorithm detects events known as "marijuana mountains", having the form of a large movement "pulling away" from the baseline, often with short-term reversals of the "slopes of the mountain" (or at least points of inflection). For example, and with reference to FIG. 5, a "marijuana mountain" is identified as follows:

(1) Starting at the peak, back up until a first point is reached at which the average slope measured over three samples exceeds the lesser of:
  (a) peak height, divided by 8; and
  (b) 140 (2° per sample).

(2) Repeat step (1) for the forward direction from the peak, to thus obtain a second point. If either of the first and second points is more than 20 samples from the peak, the event is rejected as (i.e., is not) a mountain.

(3) Starting at the peak, back up until a third point is reached at which the height is one half the height of the peak. If this involves more than 50 samples away from the peak, the event is rejected as a mountain.

(4) Repeat step (3) for the forward direction from the peak, to thus obtain a fourth point, the event being rejected if the fourth point is more than 50 samples away from the peak.

(5) If the total of samples between the third and fourth points is greater than 16, the event is classified as a mountain.

In reaching a marijuana conclusion for a given set of the standardized and calibration-corrected four runs, the following data and criteria are presently used:
  (1) The number of nystagmus events, cumulative for all four of the runs;
  (2) The number of saccade events, cumulative for all four of the runs;
  (3) The average amplitude of the two runs having the largest individual average amplitudes;
  (4) The ratio of number of nystagmus to number of saccades;
  (5) The mean amplitude of all four of the runs;
  (6) The "fast time" i.e., the number of samples for which the velocity exceeds 10 counts per sample ($\sim 4°$/sec.);
  (7) The number of saccades occurring within 20 samples of the end of the previous slow phase of a nystagmus ("SINCE");
  (8) The average slow-phase velocity of those events with SINCE$<20$; and
  (9) The average fast-phase amplitude of those events with SINCE$<20$.

Discrimination between marijuaua (MA) and normals (NO) is achieved by establishing an 8-dimensional "surface" in 9-dimensional space such that all normals appear on one side of the "surface" and all marijuanas on the other side. This is illustrated by the two-dimensional display of FIG. 5A, wherein the "surface" appears as an inclined straight line. An unknown trial is established as MA or NO by computing its Euclidian distance from the "surface"; a negative distance implies NO, and a positive distance implies MA. The location of the "surface" is based on the standard deviation for each parameter corresponding to each dimension of the space. The final conclusion is:

MA "suspected", if one or more mountains is found, or if "distance" is >2.5.

MA "present", if "distance" is >2.7.

Cocaine detection is based on the identification of pulse-like events with half-sinusoidal form, such as shown in FIG. 6A. Often these events come in groups which appear as ripples, as in FIG. 6B. Specifically, these events are characterized by (a) sinusoidal form, (b) freedom from noise, saccades, flat spots and reversals, and (c) a half-period of 0.2 to 0.5 second. FIG. 6C graphically displays such an event, with identification of relevant parameters, defined as follows:

SINCE—time since last event, measured peak-to-peak;
AMPL—average amplitude of events;
PER—average period of events;
REV—number of reversals (greater than ±4 counts);
RATIO—ratio of left (L) to right (R) areas for each side of the peak in a given half-sinusoidal event.
SHAPE—RMS error of measured event pulse as compared to a true half-sinusoid having the same amplitude and period.

The SPREAD of a given parameter is taken as STANDARD DEVIATION, divided by the MEAN.

For a cocaine conclusion, all parameters and their spreads within the runs of a given set of four must fall within the bounds tabulated below, in order to establish the "present" or "suspected" condition as to cocaine:

|  | PRESENT | | | | SUSPECTED | | | |
| --- | --- | --- | --- | --- | --- | --- | --- | --- |
|  | PARAMETER | | SPREAD | | PARAMETER | | SPREAD | |
|  | MIN | MAX | MIN | MAX | MIN | MAX | MIN | MAX |
| SINCE | 10.2 | 17.5 | 0.725 | 0.925 | 10.2 | 19.3 | 0.625 | 0.925 |
| AMPL | 52 | 96 | 0.555 | 1.575 | 52 | 96 | 0.525 | 1.575 |
| PER | 6.9 | 11.0 | 0.165 | 1.125 | 6.8 | 15.9 | 0.585 | 1.125 |
| REV | 1.9 | 3.2 | 0.815 | 1.065 | 1.9 | 3.9 | 0.815 | 1.125 |
| RATIO | 1.0 | 1.25 | 0.455 | 0.815 | 1.0 | 1.9 | 0.455 | 0.815 |
| SHAPE | 0.56 | 0.60 | 0.155 | 0.365 | 0.56 | 0.60 | 0.155 | 0.365 |

What is claimed is:

1. Apparatus for the non-invasive determination whether or not a subject has ingested a particular suspected single drug, said apparatus comprising:
    (a) plural electodes adapted for placement in the temple region of the subject's head, and ENG means connected to said electrodes for producing an electronystagmograph waveform for the subject;
    (b) said ENG means including an amplifier and analog-to-digital converter means for converting said waveform into a digitally recorded waveform for digital processing;
    (c) a digital computer with digital-storage means, wherein said storage means contains digitally stored reference data uniquely characterizing each of a plurality of waveform-component features for said single drug; and
    (d) means coacting with said computer for comparing the subject's digitally recorded waveform for possible correlation with the digitally stored reference data for each of said component features.

2. Apparatus for the non-invasive detection of drug ingestion by a subject, said apparatus comprising:
    (a) plural electrodes adapted for placement in the temple region of the subject's head, and ENG means connected to said electrodes for producing an electronystagmograph waveform for the subject;
    (b) said ENG means including an amplifier and analog-to-digital converter means for converting said waveform into a digitally recorded waveform for digital processing;
    (c) a digital computer with digital-storage means, wherein said storage means contains stored reference data uniquely characterizing each of a plurality of waveform-component features for each of a plurality of different ingested drugs;
    (d) means coacting with said computer for comparing, for possible correlation, the subject's digitally recorded waveform with the digitally stored reference data for each of said component features, whereby specific identification of one or more of said different drugs may be made from evaluation of one or more such correlations; and
    (e) means for indicating the drug or drugs for which such correlation is found.

3. Apparatus according to claim 2, in which said indicating means includes means indicating the extent of correlation.

4. Apparatus according to claim 2, in which the recorded waveform includes the waveform for a calibration run, said stored reference data being standardized to a predetermined norm, and said (d) means further coacting with said computer for converting the subject's calibration-run data to the scale of said predetermined norm preparatory to comparing the subject's digitally recorded waveform with the digitally stored reference data.

5. Apparatus according to claim 4, in which the calibration run is for eyes open with tasking.

6. Apparatus according to claim 2, in which the at-rest conditions of said standardized set include (i) eyes closed right, (ii) eyes closed left, (iii) PAN right, and (iv) PAN left.

7. A non-invasive method of using a digital computer to detect drug ingestion by a subject, said method comprising the steps of:
    (a) entering into computer storage digital reference data that are characteristic of each of a selected plurality of component features of time-varying fluctuations in an electronystagmograph waveform for each of a plurality of different ingested drugs, wherein the selected component features exist within a standardized set of at-rest conditions of electronystagmograph waveforms, the plurality of component features being selected such that each of the drugs is characteristically identifiable by the presence of its singular combination of said component features;

(b) non-invasively measuring the subject's waveform, by digitally recording time-varying fluctuations in the electronystagmograph waveform, for each of the at-rest conditions of said standardized set; and (c) comparing the subject's digitally recorded waveform with the digitally stored reference data for each of said component features to ascertain whether there exists any correlation therebetween, thereby determining the presence or absence in the subject's waveform of a particular drug-identifying combination of said component features.

8. The method of claim 7, in which the at-rest conditions of said standardized set include (i) eyes closed right, (ii) eyes closed left, (iii) PAN right, and (iv) PAN left.

9. The method of claim 7, in which the stored digital reference data are standardized to a predetermined norm of waveform calibration reference, and in which a non-invasive measurement is digitally recorded in a calibration run for eyes open, with tasking, and in which the waveform for the calibration run is used to convert to said predetermined norm the measurements of step (b) for use in making the comparisons of step (c).

10. The method of claim 7, in which the computer-storage entries of step (a) are part of an on-going database accumulation for each of the plurality of ingested drugs, and in which, after determining the presence of a particular drug-identifying combination of said component features, the subject's digitally recorded data for his drug-identifying combination of component features are entered into computer storage as an accretion to the data base.

11. The method of claim 7, wherein the plurality of different ingested drugs of step (a) includes at least one from the group consisting of alcohol, marijuana, cocaine, an opiate, and a hallucinogen.

12. The method of claim 7, wherein component features of step (a) comprise activity close to the baseline, whereby the group comprising opiates, cocaine and hallucinogens may be segregated from other drug groups.

13. The method of claim 12, wherein the recorded waveform is analyzed for the presence of a 5–6 Hz "buzz" activity, whereby a hallucinogen condition is identified by the presence of said "buzz" activity, and an opiate or cocaine condition is indicated by the absence of said "buzz" activity.

14. The method of claim 13, wherein the recorded waveform is analyzed for the presence of flat spots with small rapid movements therebetween, whereby an opiate condition is identified by said presence of flat spots with small rapid movements therebetween.

15. The method of claim 13, wherein the recorded waveform is analyzed for the presence of bimodal (combined low- and mid-frequency ripples), whereby a cocaine condition is identified.

16. The method of claim 7, wherein component features of step (a) comprise plural nystagmus events, whereby pathology, alcohol and marijuana may be segregated from other drug groups.

17. The method of claim 16, wherein the recorded waveform is analyzed for plural nystagmus events having the following characteristics:
mostly "heads",
mostly with a period of 0.5 to 3 seconds,
mostly in the PAN position,
slow-phase returning consistently toward the baseline,
tendency to exponential decay in the slow phase,
tendency toward noise in the slow phase, and
waveform "leaning" in the direction of the head,
whereby an alcohol condition is identified.

18. The method of claim 16, wherein the recorded waveform is analyzed for plural saccades having the following characteristics:
mixed "heads" and "tails",
mostly with a period of 0.5 to 5 seconds,
new saccades often interrupting the slow phase of the previous saccade,
slow phase often not returning to the baseline,
tendency to a straight-line slow phase,
tendency toward no noise in the slow phase, and
waveform having "mountainous shapes" or not "leaning" in either direction, whereby a marijuana condition is identified.

19. The method of claim 16, in which the nystagmus events are characterized by a plurality of slow-phase data points and in which the leaning ratio is greater than unity in the PAN-right position and less than unity in the PAN-left position, whereby an alcohol-indicative condition is probable.

20. The method of claim 19, in which the number of slow-phase data points is at least substantially 280, and in which the leaning ratio is greater than 1.045 in the PAN-right position, and less than 0.895 in the PAN-left position, whereby to achieve at least substantially a 90 percent probability of alcohol-identifying accuracy.

21. The method of claim 7, wherein component features of step (a) comprise plural large pendula movements away from the baseline, whereby amphetamines, tranquilizers and barbiturates may be segregated from other drug groups.

22. The method of claim 21, in which the recorded waveform is analyzed for the presence of plural triangular movements, whereby a tranquiziler condition is identified.

23. The method of claim 22, in which the recorded waveform is additionally analyzed for the absence of mid- or high-frequency noise superposed on low-frequency activity, whereby greater assurance is had as to absence of a barbiturate condition.

24. The method of claim 21, in which the recorded waveform is analyzed for the presence of mid- or high-frequency noise superposed on low-frequency activity, whereby a barbiturate condition is identified.

25. The method of claim 24, in which the recorded waveform is additionally analyzed for the absence of triangular movements, whereby greater assurance is had as to absence of a tranquilizer condition.

* * * * *

UNITED STATES PATENT AND TRADEMARK OFFICE
CERTIFICATE OF CORRECTION

PATENT NO. : 4,715,386

DATED : December 29, 1987

INVENTOR(S) : Peter G. Martin, S. Thomas Westerman, Liane M. Gilbert

It is certified that error appears in the above-identified patent and that said Letters Patent is hereby corrected as shown below:

ON THE TITLE PAGE, ITEM [75] should read

-- [75] Inventors: Peter G. Martin, Mercer Island, Wash.,
S. Thomas Westerman, Shrewsbury, N.J., and
Liane M. Gilbert, Monmouth Beach, N.J. --.

Signed and Sealed this

Twenty-fourth Day of May, 1988

*Attest:*

DONALD J. QUIGG

*Attesting Officer*  *Commissioner of Patents and Trademarks*